(12) United States Patent
Van Rijn et al.

(10) Patent No.: US 11,998,685 B2
(45) Date of Patent: Jun. 4, 2024

(54) SPRAY DEVICE, SPRAY UNIT AND SPRAY CARTRIDGE

(71) Applicant: MEDSPRAY B.V., Enschede (NL)

(72) Inventors: Cornelis Johannes Maria Van Rijn, Amsterdam (NL); Wietze Nijdam, Enschede (NL); Henri Joseph Van Egmond, Enschede (NL); Wilhelmus Petrus Johannes De Kruijf, Enschede (NL)

(73) Assignee: MEDSPRAY B.V., Enschede (NL)

( * ) Notice: Subject to any disclaimer, the term of this patent is extended or adjusted under 35 U.S.C. 154(b) by 0 days.

(21) Appl. No.: 17/041,913

(22) PCT Filed: Mar. 26, 2019

(86) PCT No.: PCT/NL2019/050188
§ 371 (c)(1),
(2) Date: Sep. 25, 2020

(87) PCT Pub. No.: WO2019/190316
PCT Pub. Date: Oct. 3, 2019

(65) Prior Publication Data
US 2021/0008577 A1    Jan. 14, 2021

(30) Foreign Application Priority Data

Mar. 26, 2018    (NL) ..................... 2020671

(51) Int. Cl.
*A61M 15/00*    (2006.01)
*A24F 40/05*    (2020.01)
(Continued)

(52) U.S. Cl.
CPC ............ *A61M 15/06* (2013.01); *A24F 40/05* (2020.01); *A24F 40/48* (2020.01); *A24F 42/20* (2020.01);
(Continued)

(58) Field of Classification Search
CPC .. A61M 11/00; A61M 11/003; A61M 11/006; A61M 11/007; A61M 11/02;
(Continued)

(56) References Cited

U.S. PATENT DOCUMENTS

| | | | | |
|---|---|---|---|---|
| 5,437,267 A | * | 8/1995 | Weinstein | A61M 15/009 128/200.23 |
| 6,189,813 B1 | * | 2/2001 | Skeath | B05B 7/0433 261/78.2 |

(Continued)

FOREIGN PATENT DOCUMENTS

| | | |
|---|---|---|
| EP | 1005916 A1 | 6/2000 |
| GB | 2524856 A | 10/2015 |
| WO | WO-2014150131 A1 | 9/2014 |

OTHER PUBLICATIONS

ISA/EP, International Preliminary Report on Patentability (Chapter II), dated Jul. 28, 2020 re PCT International Patent Application No. PCT/NL2019/050188.

*Primary Examiner* — Annette Dixon
(74) *Attorney, Agent, or Firm* — Perry + Currier Inc.

(57) ABSTRACT

The invention relates to a spray device having a spray nozzle unit and at least one further spray nozzle unit. Each spray nozzle unit has at least one spray nozzle body, wherein at least one spray nozzle body comprises a chamber for receiving a pressurized fluid. The chamber is bound by a spray wall having at least one spray orifice that extends through the spray wall and opens to an external environment. Each of at least one orifice in a spray wall has a substantially identical predetermined size lying in a predetermined range and releases a mono disperse spray jet of the pressurized fluid fed from the associated reservoir. The range within the first spray nozzle unit differs from the range within at least one further spray nozzle unit; particularly, the ranges do not overlap.

14 Claims, 2 Drawing Sheets

(51) Int. Cl.
    *A24F 40/48*     (2020.01)
    *A24F 42/20*     (2020.01)
    *A24F 42/60*     (2020.01)
    *A61M 11/00*     (2006.01)
    *A61M 15/06*     (2006.01)
    *B05B 7/08*     (2006.01)
    *B05B 7/24*     (2006.01)
    *A24F 40/10*     (2020.01)

(52) U.S. Cl.
    CPC .......... *A24F 42/60* (2020.01); *A61M 11/006* (2014.02); *A61M 15/0003* (2014.02); *A61M 15/009* (2013.01); *B05B 7/0846* (2013.01); *B05B 7/2467* (2013.01); *A24F 40/10* (2020.01)

(58) Field of Classification Search
    CPC ................ A61M 11/042; A61M 11/06; A61M 15/0003; A61M 15/0005; A61M 15/0021; A61M 15/0065; A61M 15/0068; A61M 15/009; A61M 15/08; A61M 16/201; A61M 2202/0208; A61M 2202/025; A61M 2202/0266; A61M 2202/04; A61M 2202/0484; A61M 2205/3334; A61M 2205/3653; A61M 2205/368; A61M 2205/502; A61M 2205/505; A61M 2205/581; A61M 2205/583; A61M 2205/7545; A61M 2205/8281; A61M 2207/00; A61M 2210/0618; A61M 2230/005; A61M 35/00; A62B 23/06; A62C 31/05; A62C 37/11; B05B 1/14; B05B 1/1618; B05B 1/169; B05B 1/26; B05B 1/267; B05B 1/3006; B05B 11/0005; B05B 11/00412; B05B 11/007; B05B 11/0089; B05B 11/3001; B05B 11/308; B05B 11/3091; B05B 15/40; B05B 15/55; B65D 83/7535; B81B 2201/054; F16K 7/17; Y10T 29/49826

See application file for complete search history.

(56) References Cited

U.S. PATENT DOCUMENTS

| | | | | |
|---|---|---|---|---|
| 10,632,265 | B2* | 4/2020 | Van Egmond | B05B 15/40 |
| 2005/0263618 | A1* | 12/2005 | Spallek | A61M 15/0003 |
| | | | | 239/433 |
| 2006/0118107 | A1* | 6/2006 | King | A61M 15/0005 |
| | | | | 128/200.23 |
| 2013/0199521 | A1* | 8/2013 | Hausmann | A61M 15/009 |
| | | | | 128/200.23 |
| 2016/0045682 | A1* | 2/2016 | Boyden | A61M 11/02 |
| | | | | 128/200.19 |
| 2018/0353977 | A1* | 12/2018 | Nijdam | B65D 83/7535 |
| 2018/0353980 | A1* | 12/2018 | Van Rijn | A62C 37/11 |
| 2021/0059301 | A1* | 3/2021 | Hejazi | A24F 42/20 |

* cited by examiner

SPRAY DEVICE, SPRAY UNIT AND SPRAY CARTRIDGE

The present invention relates to a spray device, comprising a first spray unit, said first spray unit comprising a spray nozzle unit in fluid communication with a first reservoir for holding a quantity of a fluid to be sprayed, wherein said first spray nozzle unit comprises a first spray nozzle body with a first spray wall that is provided with at least one first spray orifice extending through a thickness of said first spray wall, said at least one first spray orifice receiving, during operation, said first fluid under pressure from said first reservoir at an inlet side and releasing a spray jet of said fluid to an external environment at a spray side, and wherein each of said at least one orifice has a substantially identical predetermined size, lying in a predetermined range, and comprising at least one further spray unit, said further spray unit comprising a further spray nozzle unit in fluid communication with a further reservoir for holding a quantity of a further fluid to be sprayed. The invention further relates to a spray cartridge to be used in such a spray device.

The present invention particularly relates to such a spray device for generating a so-called micro-jet spray. A micro-jet spray consists of a number of concurrently emitting jets, in which each jet will initially breakup into a mono-disperse primary droplet train according to a Rayleigh breakup mechanism. As a result, consecutive primary droplets have a same size and propagate from the spray orifice in a same direction, typically the diameter of the primary droplet is between 1.85 and 2 times the diameter of the spray orifice. Often the spray orifices are provided in a planar spray wall yielding jets that are all directed in a same spraying direction. Providing the spray orifices in a curved spray wall or in a deformable substrate yields jets directed in mutually different spraying directions that may be used to control the amount of jet coalescence between adjacent jets.

For specific applications such as cosmetics, perfume, wafer cleaning, fuel injection, spray dryers, medical sprays, characteristic spray patterns are required and adequate control of the droplet size distribution of the generated spray is required. For respiratory pharmaceutical applications, for instance, a spray providing small droplets with a narrow size distribution can be efficiently targeted at different sections of the lungs, provided that the micro-jet spray can be controlled and reproduced adequately. The spray device in that case may serve as an inhaler for personal use.

A spray device is for instance known from WO02/18058. This known spray device comprises a spray nozzle unit that uses one or more silicon bodies for generating a micro-jet spray. A membrane layer of silicon nitride, overlying the silicon body, is locally perforated using ultra precise semiconductor technology, like photo-etching, to form a plurality of spray orifices that have substantially an identical cross section. The silicon body is locally etched underneath said orifices to establish a cavity that forms a chamber for receiving the fluid to be sprayed under pressure. As a result the fluid is forced out of the chamber through said orifices to enter into the environment as a train of substantially equal droplets, each having a size of between 1.85 and 2 times a dimeter of the orifice from which it emanated.

Although this known device is particularly useful for targeting a particular unique treatment, at the same time it is also limited to targeting that particular application. In practice, however, there is sometimes a need for a spray device that is capable of suiting more than a single target. For medical and pharmaceutical applications, particularly, it would be desirable to have a spray device that targets a certain medical condition, while on the other hand counteracting unwanted side effects.

A spray device of the type described in the opening paragraph for targeting different areas in the respiratory system is known from UK patent application GB 2.524.856. This known sprat device contains a first chamber adapted to thermally vaporise a quantity of a first liquid to form a relatively warm first vapour. The device further contains a second chamber adapted to atomize a quantity of a second liquid to form a mist of a relatively cold second vapour. A user may inhale a mixture of both vapours through a common outlet of the device. An active ingredient such as nicotine may be provided in the second chamber and an inert liquid like a water-glycol mixture may be used as the first liquid in the first chamber. In this manner, a rapid absorption of said active ingredient contained in the second vapour may be achieved while providing the user with a desirable heat sensation on inhalation provided by the warm first vapour as soon as this vapour hits the oral cavity.

The latter device intends to provide an alternative for a traditional cigarette, targeting the lungs specifically with the second vapour, containing nicotine, while the warm vapour merely gives a neutral heat sensation. The usefulness of this device as a replacement for a traditional cigarette, however, is limited as it does not provide for further active ingredients in the first vapour like fragrances, flavourings, or pigments to identify and characterize the product in a sense of taste and aroma appealing to the user. As the known device cannot avoid that this warm vapour might reach the lungs such active components cannot be added without a risk of adversely affecting the condition of the respiratory system, notably the lungs.

The present invention has inter alia for its object to provide a spray device that offers a solution in this respect.

In order to achieve said goal a spray device of the type as described in the opening paragraph is, according to the invention, in a first aspect characterized in that said further spray nozzle unit comprises a further spray nozzle body with a further spray wall that is provided with at least one further spray orifice extending through a thickness of said further spray wall, said at least one further spray orifice receiving, during operation, said further fluid under pressure from said further reservoir at an inlet side and releasing a spray jet of said further fluid to an external environment at said spray side, wherein each of said at least one further orifice has a substantially identical further predetermined size, lying in a further predetermined range that differs from said first predetermined range of said at least one first orifice of said first nozzle body of said first spray unit. The spray device according to the invention, hence, comprises a further spray nozzle unit with further spray orifices, similar to the first nozzle unit, however with a further predetermined size for said one or more further orifices that differs from the predetermined (first) size of the at least one first orifices.

This further orifice size is useful for targeting another (or same) fluid on the same or a different area, depending on the droplet size of the jet spray that is therewith created. Smaller droplets may spread out more easily, will have lesser impact on said surface and/or may be carried further by a prevailing air stream. Droplets having more volume, on the other hand, will be drawn less far and give more impact at a same velocity. By having dual or more perforated spray walls that are dimensioned and configured individually and are supplied from a separate reservoir, the spray device of the invention offers an unsurpassed flexibility and an extra dimension allowing it to be tailored towards a variety of new and improved medical and non-medical spray treatments, uses and therapies.

In a further aspect of the invention, a spray device comprising at least one spray nozzle unit having at least one spray nozzle body, wherein said at least one spray nozzle body comprises a chamber for receiving a pressurized fluid and said chamber is bounded by a spray wall having at least one nozzle orifice that extends through said spray wall and opens to an external environment, wherein each of said at least one orifice has a substantially identical predetermined size lying in a predetermined range, wherein said at least one nozzle orifice is configured and intended to release a spray jet of a spray to be generated by said spray nozzle unit, and wherein, during operation, said at least one nozzle body of said spray unit is fed with said pressurized fluid from a reservoir containing a quantity of said fluid, is characterized in that said spray device comprises at least one further spray nozzle unit having at least one further spray nozzle body, wherein said at least one further spray nozzle body comprises a chamber for receiving a further pressurized fluid and said chamber is bounded by a further spray wall having at least one further nozzle orifice that extends through said of said spray wall and opens to an external environment, wherein each of said at least one further orifice has a substantially identical further predetermined size lying in a further predetermined range, wherein said at least one nozzle further orifice is configured and intended to release a spray jet of a further spray to be generated by said further spray nozzle unit, wherein, during operation, said at least one further nozzle body of said further spray unit is fed with said further pressurized fluid from a further reservoir containing a quantity of said further fluid, and wherein said predetermined range of said predetermined size of said at least one orifice differs from said further predetermined range of said further predetermined size of said at least one further orifice.

In a preferred embodiment the spray device according to the invention is characterized in that actuator means are provided that are manually operable to force said fluid and said further fluid under pressure to said nozzle unit and said further nozzle unit respectively. As such the spray device is provided with actuator means that act jointly on both said first reservoir with said first fluid and on said at least one further reservoir with said at least one further fluid. This enables a dual or multiple therapy or treatment with said first fluid and said at least one further fluid in a single action by the user.

In order to avoid under dosing or overdosing of one or all fluids concerned, a specific embodiment of the spray device according to the invention is characterized in that said actuator means are configured and intended to charge and release a dosed quantity of said fluid in a predetermined amount. The spray device in that case has a self-dosing mechanism that releases an appropriate quantity of fluid each time it is triggered. This mechanism may be powered in different ways. A specific embodiment of the spray device according to the invention is characterized in that sense in that said actuator means are energized by means of a tensioned spring, electrical power or manual operation.

A further preferred embodiment of the spray device according to the invention is characterized in that said first spray unit and said further spray unit are both removably accommodated in said spray device. A preferred embodiment of the spray device according to the invention is thereby characterized in that said first spray unit and said second spray unit are part of a spray cartridge that is removably fitted in said spray device. This facilitates a convenient replacement, exchange, or refill of the fluids by simple exchange of a joint cartridge. In a particularly user friendly embodiment said spray device is characterized in that said first spray unit and said second spray unit engage said actuator means upon insertion in said spray device. In this case a simple placement of the cartridge suffices to render the device fully operable.

Although a wide variety of materials may be employed for the nozzle bodies, particularly satisfactory results have been achieved with a specific embodiment of the spray device according to the invention that is characterized in that said first and further nozzle body are made of a material from a group containing semiconductor materials, glass, metals, ceramics and polymers, more particularly in that said nozzle bodies comprises a semiconductor body, and preferably in that said nozzle bodies comprises a silicon body, particularly of mono-crystalline silicon. Especially the latter material allows the use of existing silicon processing techniques and appears to render a pray device that is both durable and re-reproducible.

In practice there is a demand for a spray device capable of generating mono-disperse micro jets. Such micro-jets consist of rays of relatively small droplets of substantially identical size ranging from a few micron to a few tens or hundreds of microns. This requires the orifices to be formed with an equal, or at least comparable, amount of precision. To that end, a further preferred embodiment of the spray device according to the invention is characterized in that said spray wall comprises a layer of a material that is compatible with a semiconductor manufacturing process for said semiconductor body, particularly a material taken from a group of silicon, silicon nitride and silicon oxide.

More particularly a further embodiment is thereby characterized in that said at least on orifice and said at least one further orifice are created by means of a semiconductor manufacturing process technique, particularly by photo lithographically etching, or a micro-machining technique. Using such material for said spray layer allows the use of sophisticated existing semiconductor technology for realizing the spray orifices with an extremely high degree of accuracy resulting in exceptionally tight tolerances. This in turn will result in a strict mono-disperse nature of the droplets emanating from these orifices.

In order to be able to reach mutually excluding target areas by a spray of the first fluid and a spray of the further fluid, a further specific embodiment of the spray device according to the invention is characterized in that said first range and said further range have substantially no overlap. The first range will in that case lead to formation of droplets around a first size, whereas the second range of the further nozzle body will deliver droplets around a different size. These droplets will then follow different trajectories once they have escaped from their originating orifice and have different effective cross-sections and hence collision probabilities, both depending on their size. All in all, this will lead to different landing spots of both sprays that may be generated concurrently or consecutively by the spray device. By choosing the amount of orifices on both spray walls in relation to their total occupied surface area in combination with the flow rate and pressure of the fluid concerned, the exact nature of the generated sprays may be optimized even further.

A specific embodiment of the spray device according to the invention is therefore characterized in that said first range is a range between 2 micron and 5 micron and in that said further range is a range beyond 5 micron, particularly said further range in a range between 5 micron and 10 micron. These ranges allow the first nozzle unit to deliver the first fluid deeply into the longs, whereas the second range will result in droplets beyond 10 micron that will be captured already in the oral cavity of the user once inhaled.

In a particular application such a spray device in characterized in that said first fluid contains nicotine as an active compound and the further fluid comprises one or more of a flavouring, pigment, or fragrance. The latter ingredients will in that case be introduced in the oral cavity only substantially without reaching the lungs, whereas the nicotine compound will be administered substantially entirely to the lungs in order to be absorbed in the blood circulation of the user. This will give both a pleasant taste, masking the bitterness of nicotine, as well as the known parasympathomimetic action that nicotine is known for, without or at least considerably less health risks that associated with classical cigarettes and many electronic cigarette replacements or alternatives that lead to both nicotine and possibly toxic compounds reaching the lungs.

In a particular application such a spray device in characterized in that said first fluid contains a pharmaceutical compound and the further fluid comprises one or more of a flavouring or fragrance. The latter ingredients will in that case be introduced in the oral cavity only substantially without reaching the lungs, whereas the pharmaceutical compound will be administered substantially entirely into the lungs in order to be absorbed in the blood circulation of the user. The flavouring or fragrance may then compensate or camouflage a tasteless, unappetizing or even revolting nature of the effective medicinal product without having an effect in or on the lungs. As a further or alternative effect, the second spray will give the user a noticeable feedback that a spray was actually introduced which is particularly important when only a small dose of the first fluid needs to be inhaled with a risk of overdosing.

Also, multiple or combined therapeutic effects may be realized with the spray device according to the invention by means of one or more first pharmaceuticals as an active compound of the first fluid in combination with one or more further pharmaceuticals in the second fluid. Specifically, the first fluid contains corticosteroids that have an optimal effect when introduced deeply into the lungs and the second fluid is a bronchial dilatation agent that widens the tracheal system to give way to a spray of the first fluid. A specific field of application of such a device may be an inhaler for treating respiratory conditions, like asthma or cystic fibrosis, employing a tracheal introduction of specific pharmaceutical or other active components.

A specific embodiment of the latter kind is characterized in that said first range is a range between 1.5 micron and 2.5 micron and in that said further range is a range beyond 3 micron, particularly said further range in a range between 3 micron and 4 micron. This device is particularly useful for treating respiratory conditions, like asthma or cystic fibrosis. The corticosteroid droplets will reach the lungs and spread over the lungs, whereas the larger droplets of the bronchial dilatation agent cause the tracheal system to widen and to give way to the corticosteroid droplets.

The invention further relates to a spray cartridge that may conveniently be used in conjunction with any of the spray devices according to the invention as described hereinbefore. Such a spray cartridge, for removably fitting in such spray device, comprises said first spray unit and said at least one further spray unit, said first spray unit having said at least one spray orifice in said first predetermined range and said further spray unit having said at least one further spray orifice in said further predetermined range, said first and second predetermined range being distinct, in particular without overlapping one another.

In a particular embodiment the spray cartridge according to the invention is characterized in that said first range is a range between 2 micron and 5 micron and in that said further range is a range beyond 5 micron, particularly said further range in a range between 5 micron and 10 micron. The sizes of the orifices render the cartridge particularly useful as a replacement for a traditional cigarette. To that end a preferred embodiment of the cartridge is characterized in that said first spray unit comprises said first reservoir being at least partly filled with a first fluid, containing nicotine as an active compound, and in that said further spray unit comprises said further reservoir being at least partly filled with said second fluid, containing one or more of a fragrance, flavouring and pigment.

The invention will now be described in further detail with reference to one or more embodiments and an accompanying drawing. In the drawing.

Figure 1:
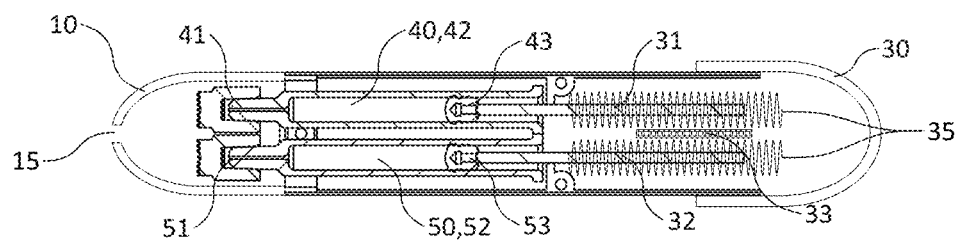
FIG. 1 shows a cross section of a first example of a spray device according to the invention.
Figure 2:
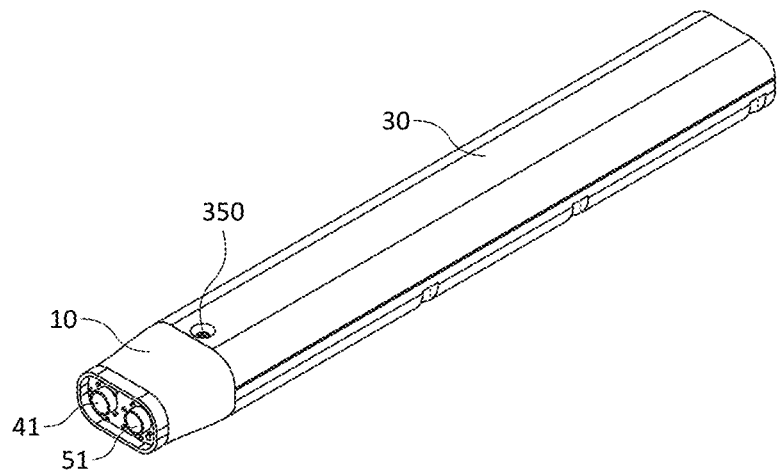
FIG. 2 shows a perspective view on a second example of a spray device according to the invention.
Figure 3:
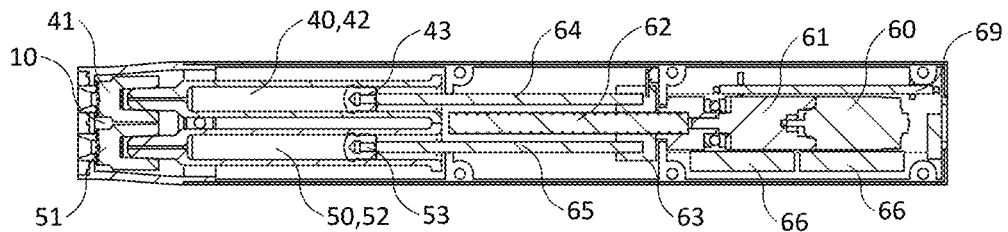
FIG. 3 is a cross section of the spray device of FIG. 2.
Figure 4:
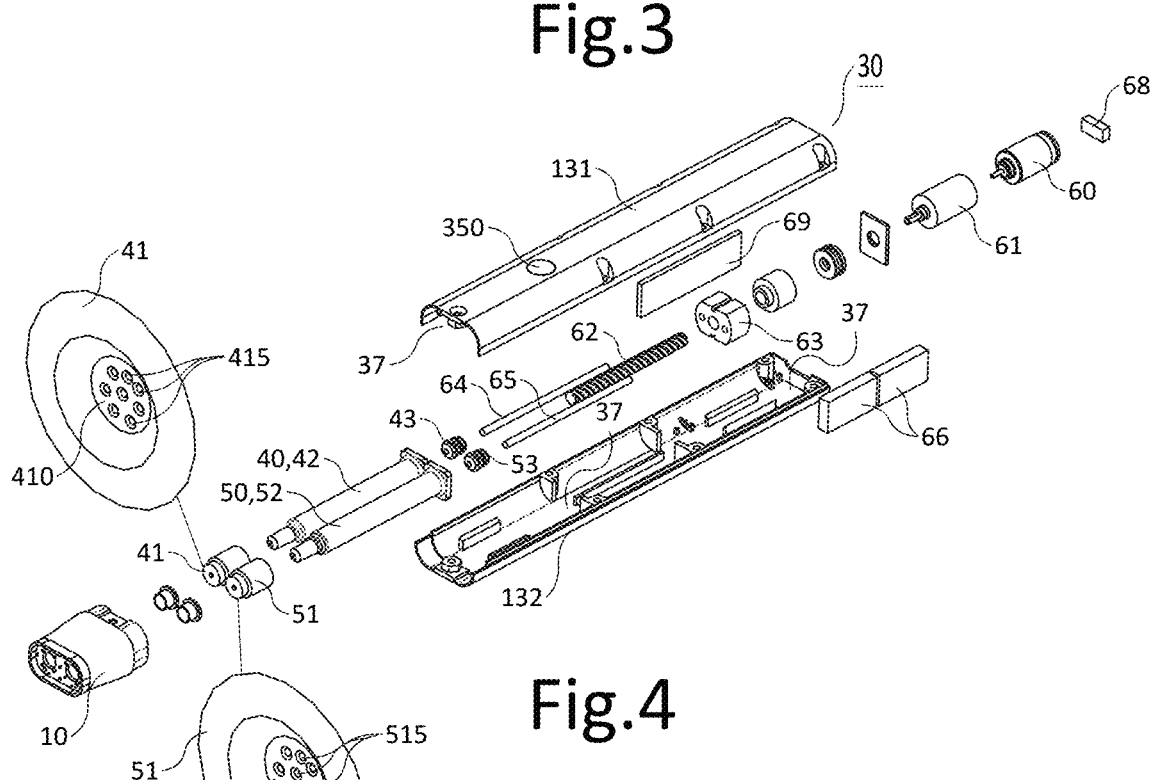
FIG. 4 is an exploded view of the spray device according to FIG. 2.
Figure 5:
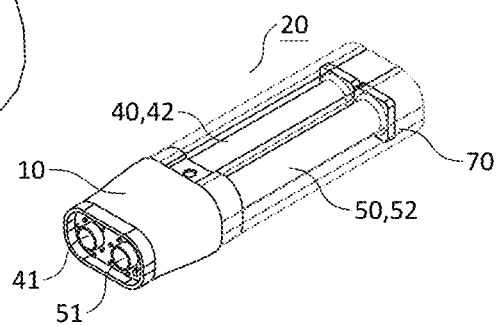

FIG. 5 is a perspective view of a spray cartridge to be used in any of the spray devices of FIGS. 1 and 2. It should be noted that the figures are purely schematically and not drawn to (a same) scale. In particular certain dimensions may be exaggerated to a greater or lesser extent for sake of clarity. Corresponding parts are denoted by same reference numerals throughout the drawing.

FIG. 1 schematically shows an example of a spray device according to the present invention. In this case the spray device is a respiratory inhaler that may be used to administer one or more active compounds into the lung of the user. As such the device comprises a mouth piece 10 at one end and a grip member 30 at an opposite end. The device may be taken and manually operated by the grip member 30, whereas the mouth piece 10 is intended and configured to be partially introduced into the oral cavity of the user, to be held between the lips. The mouth piece 10 is detachable in order to be easily cleanable. Besides for releasing the active compound(s) and providing an outlet opening 15, the mouth piece 10 moreover serves as a mixing chamber in which environmental air is drawn upon breath activation of the device by the user.

At the heart of the device is a spray cartridge 20. The spray cartridge 20 is detachable from the grip member 30 and releasably connected to the mouthpiece 10. The spray cartridge contains a first spray unit 40 and a further spray unit 50. Each spray unit comprises a spray nozzle unit 41,51, often referred to as spray head, that comprises a dedicated spray nozzle device. Each spray unit further comprises a reservoir in the form of a syringe 42,52 that holds a quantity of a certain fluid (liquid) to be sprayed by the corresponding spray unit. A bottom of each reservoir is formed by a plunger 43,53 that is axially displaceable within the reservoir in order to expel liquid from said reservoir and to force it under pressure to the corresponding spray nozzle unit 41,51.

Upon insertion of the cartridge 20 in the device, said plungers will engage actuator means 35 that comprises a set of compression springs 31,32 in the grip member 30 that are compressed by turning the grip member 30 relative to the cartridge 20 holding portion of the device. This spring drive actuation is stepwise, each step corresponding to a single dose of each liquid to be sprayed. A dose indicator 33 informs the user of the remaining number of doses still available in the device. Both springs 31,32 may exert a same spring force on both plungers 43,53 or may be tensioned differently to provide an individual spring force for each spray unit 40,50. Also by varying the surface area of the plungers 43,53 more or less pressure may be exerted on the fluid under influence of the same spring force. Particularly the pressure put on the pressurized fluid may depend on the pore size of the orifices as a larger pore size will generally require a lower pressure for an optimal spray image.

In this particular example, the first syringe 42 within the first spray unit 40 holds a liquid containing nicotine as an active compound. The spray nozzle unit 41 mounted on this spray unit comprises a silicon nozzle body, having a perforated spray wall of silicon nitride overlying one or more cavities that are provided within the nozzle body for receiving the first fluid under pressure. The perforations in said spray wall, as well as said cavities, are created using ultra precise semiconductor technology or MEMs technology, delivering orifices in said spray wall of approximately a same size. In this case the orifices are etched using photolithography with a predetermined size of between 2 and 5 micron, more specifically with a circular cross section of a diameter around and average of 2.5 micron within a tolerance of less than 20%, particularly less than 10%. The first spray unit, as a result, will deliver a mono disperse spray of nicotine containing droplets having a average of around 5 micron. These droplets will easily reach the lungs of the user to give a parasympathomimetic sensation that nicotine and cigarettes are known for.

The second syringe 52 within the second spray unit 50 holds a further liquid that contains one or flavourings and fragrances. The further spray nozzle unit 51 mounted on this spray unit 50 comprises a silicon nozzle body, having a perforated spray wall of silicon nitride overlying one or more cavities that are provided within the nozzle body for receiving the first fluid under pressure. The perforations in said spray wall, as well as said cavities, are created using ultra precise semiconductor technology or MEMs technology, delivering orifices in said spray wall of approximately a same size. In this case the orifices are etched using photolithography with a predetermined size of between 5 and 10 micron, more specifically with a circular cross section of a diameter around and average of 7.5 micron within a tolerance of less than 20%, particularly less than 10%. The second spray unit 50, as a result, will deliver a mono disperse spray of nicotine containing droplets having a average of around 15 micron. These droplets will not, or hardly not, reach the lungs but will be almost completely captured by the oral cavity.

FIG. 2 shows a second embodiment of a spray device according to the invention. This embodiment resembles to a large extent the first embodiment, but in this example the actuator means are electrically drive instead of operating based on spring force. The device consists of a grip member 30 and a detachable mouth piece 10. A first spray nozzle unit 41 and a second spray nozzle unit 51 open into the mouth piece that guides both sprays that are released by these spray nozzle units 41,51 into the oral cavity. The device may be energized by means of a push/touch button 350 on the gripping member to be pressed or touched by the user. Alternatively a flow sensor, pressure sensor or other registration means may be integrated at the entrance of the mouth piece 10 to record a suction action by the user and upon such action to energize the device. The grip member 30 has typically a length and width of less than 200 millimetre and less than 15-20 millimetre respectively, closely resembling those of a big cigar. This part of the device accommodates all essential components, apart from the mouth piece, as may become apparent from the cross section of FIG. 3 and the exploded view of FIG. 4.

The grip member 30 is formed by a top shell portion 131 and bottom shell portion 132 that enclose a longitudinal cavity 37. A removable spray cartridge 20 sticks into said cavity at one end to engage a pair of drive members 64,65. The spray cartridge 20 is shown in greater detail in FIG. 4 and may have a plastic shell 70 removably fitting in a bay that is formed by the open end of the cavity 37. The spray cartridge comprises a first spray unit 40 and a second spray unit 50. Each of the spray units 40,50 comprises a glass or plastic syringe 42,52 containing typically between 0.5 and a few millilitre of a first fluid and a second fluid respectively. Thereby the first fluid is a nicotine containing neutral solution. The second fluid, however, may comprise one or more of a fragrance, flavouring and pigment. This gives the product a distinctive taste, aroma and character. Both syringes 42,52 are closed at a bottom by a plunger 43,53 that is slidable within the respective syringe, while at the other end a first and second spray nozzle unit 41,51 are respectively mounted on the respective syringe 42,52 in open communication with the fluid.

The spray nozzle unit 41 mounted on the syringe 42 of the first spray unit 40 comprises a silicon nozzle body, see the enlarged view in FIG. 3, carrying a perforated spray wall 410 of silicon nitride with a group of spray orifices 415 overlying one or more cavities that are provided throughout a thickness of the nozzle body for receiving the first fluid under pressure. The orifices 415 in said spray wall, 410 as well as said cavities and said spray wall itself, are created using ultra precise semiconductor technology or MEMs technology, delivering these orifices 415 in said spray wall 410 of approximately a same size. In this case these orifices 415 are etched using photolithography with a predetermined size of between 2 and 5 micron, more specifically with a circular cross section of a diameter around and average of 2.5 micron within a tolerance of less than 20%, particularly less than 10%. The first spray unit 40, as a result, will deliver a mono disperse spray of nicotine containing droplets having a average of around 5 micron. These droplets will easily reach the lungs of the user to give a parasympathomimetic sensation that nicotine and cigarettes are known for.

The spray nozzle unit 51 mounted on the syringe 52 of the second spray unit 50 laso comprises a silicon nozzle body comparable to the one of the first spray nozzle unit, see the enlarged view in FIG. 3, carrying a perforated spray wall 510 of silicon nitride with a group of spray orifices 515 overlying one or more cavities that are provided throughout a thickness of the nozzle body for receiving the second fluid under pressure. The orifices 515 in said spray wall 510, as well as said cavities, are created using ultra precise semiconductor technology or MEMs technology, delivering spray orifices 515 in said spray wall of approximately a same size. In this case these second orifices 515 are etched with a predetermined size of between 5 and 10 micron, more specifically with a circular cross section of a diameter around and average of 7.5 micron within a tolerance of less than 20%, particularly less than 10%. The second spray unit 50, as a result, will deliver a mono disperse spray of droplets having a average of around 15 micron. These droplets will not, or hardly not, reach the lungs but will be almost completely captured by the oral cavity. As these droplets comprise one or more fragrances and/or flavourings, these droplets will give an attractive taste and flavour experience to the user that the user will sense with his natural olfactory receptors and taste organs in his nose and mouth.

In order to release both sprays, the device contains actuation means in the form of a stepper motor 60 connected to a gear box 61. The gear box drives a spindle 62 that engages a threaded hole in a drive block 63 for forming a screw and nut relationship. The drive block 63 has two cavities at opposite sides of the spindle 62 carrying a first drive rod 64 and a second drive rod 65 respectively. The first drive rod engages the plunger 43 of the first syringe, while the second drive rod engages the plunger 53 of the second syringe. Both plungers are provided with a conical recess at their backside to provide for a solid engagement with the drive rods 64,65. To be able to deliver sufficient force, the spindle is made of solid metal, for instance stainless steel.

The motor 60 is energized by means of a rechargeable battery pack 66 at the back of the device that may be recharged through a standard USB port 68 at the end or possibly wirelessly. The device further contains a processor unit and further circuitry on a printed circuit board 69 to control the motion of the motor 60, amongst others. On a push of the push button 350, or other activation, the motor 60 will deliver an appropriate number of cycles depending on the dose that is being desired. This dose may be among other information that is stored in memory on the PCB 69 and may be factory set or may be defined by the user. This will advance the spindle 62 a number of turns thereby driving the drive block 63 and the drive rods 64,65 carried thereby. As a result the plungers 43,53 will advance over a defined axial stroke thereby pressurizing the fluids contained in the respective syringes 42,52 and expelling the fluid out of the respective syringe. This pressure is typically between 10- and 20 bar in order to allow both spray nozzle units 41,51 to deliver a fine mist of precisely determined droplets, as described hereinbefore. In order to secure a sudden drop and rise of the pressure of the fluid, a motor 60 of quick motion type is being used and a short back stroke is imposed on the plungers at the end of a dosing. Also a pressure valve may be integrated between the syringe 42,52 and the spray nozzle unit 41,51 that will only open at a predetermined pressure within the indicated range and will suddenly shut off below such pressure.

The devices depicted in FIGS. 1 and 2 may serve as an alternative for a traditional cigarette providing a similar nicotine driven effect to the user without the health risks involved with smoking tobacco. The device moreover provides a safe and more healthy alternative for conventional cigarette replacements, like many heat-not-burn tobacco products and vaporizers, often referred to as electronic cigarettes. Contrary to those product, no suspicious components will reach the lungs of the user when using the device according to the invention.

Although the invention has been describes to merely a single specific embodiment in the preceding, it will be clear that the invention is by no means limited to that example. Instead may alternatives and variations are feasible for a skilled person without departing from the scope and spirit of the present invention, as indicated by the following claims. As an example, the spray units might also be accommodated in the spray device separately from one another, allowing for instance to change the flavour of the "cigarette" in combination with the same nicotine dispenser. Also the spray dispenser members may be dimensioned differently. Especially the reservoirs of both dispensers may have a different size (volume).

Also the actuation of the device may be effected by any other appropriate means and the device may also be used outside the framework of an electronic replacement or alternative for a conventional cigarette. The invention more in general provides a device targeting selected levels, notably in the respiratory system of the user, or a same level with different spray patterns of a same or different fluids.

The invention claimed is:

1. A spray device, comprising:
a mouth-piece,
a first spray unit oriented in said mouthpiece, said first spray unit comprising:
a first reservoir for holding a quantity of a first liquid to be sprayed, and
a first spray nozzle unit in liquid communication with the first reservoir, the first spray nozzle unit comprising:
a first spray nozzle body comprising a semiconductor body and having a first spray wall comprising a layer of material that is compatible with a semiconductor manufacturing process for said semiconductor body; and
a plurality of first spray orifices extending through a thickness of said first spray wall, wherein each of said first spray orifices has a substantially identical predetermined cross section in a first predetermined range, deviating less than 20% from an average cross section among said first spray orifices, and wherein said first spray orifices are created in said first spray wall by photo lithographically etching or a micro machining technique;
at least one further spray unit oriented in said mouthpiece adjacent said first spray unit, said at least one further spray unit comprising:
a further reservoir for holding a quantity of a further liquid to be sprayed,
a further spray nozzle unit in liquid communication with the further reservoir, the further spray nozzle unit comprising:
a further spray nozzle body comprising a further semiconductor body and having a further spray wall comprising a further layer of material that is compatible with the semiconductor manufacturing process for said further semiconductor body;
a plurality of further spray orifices extending through a thickness of said further spray wall, wherein each of said further spray orifices has a substantially identical further predetermined cross section in a further predetermined range having substantially no overlap with said first predetermined range, deviating less than 20% from a further average cross section among said further spray orifices, and wherein said further spray orifices are created in said further spray wall by the photo lithographically etching or the micro machining technique;
an actuator energized by a tensioned spring, electrical power or manual power, wherein the actuator, when activated, acts concurrently on both said first reservoir and said at least one further reservoir to force under pressure said first liquid to said first spray nozzle unit and said further liquid to said further spray nozzle unit to concurrently release a first micro-jet spray of substantially mono-disperse first droplets of said first liquid along a first pathway through said mouthpiece and a further micro-jet spray of substantially mono-disperse further droplets of said further liquid along a further pathway through said mouthpiece, the further pathway being substantially parallel to the first pathway;

wherein the mono-disperse first droplets released from the first pathway terminate in lungs of a user and are to be absorbed in blood circulation and the mono-disperse further droplets released from the further pathway terminate in an oral cavity of the user said and comprises a flavoring or fragrance.

2. The spray device according to claim 1, wherein said first spray unit and said at least one further spray unit are both removably accommodated in said spray device.

3. The spray device according to claim 2, wherein said first spray unit and said at least one further spray unit are part of a spray cartridge that is removably fitted in said spray device.

4. The spray device according to claim 2, wherein said first spray unit and said at least one further spray unit engage said actuator upon insertion in said spray device.

5. The spray device according to claim 1, wherein said first predetermined range is a range between 1.5 micron and 2.5 micron and wherein said further predetermined range is a range beyond 3 micron.

6. The spray device according to claim 5, wherein said first reservoir is at least partly filled with said first liquid, said first liquid containing a corticosteroid as an active compound, and wherein said further reservoir is at least partly filled with said further liquid, said further liquid containing a bronchial dilatation agent.

7. The spray device according to claim 5, wherein said further predetermined range is between 3 micron and 4 micron.

8. The spray device according to claim 1, wherein said first predetermined range is a range between 2 micron and 5 micron and wherein said further predetermined range is a range beyond 5 micron.

9. The spray device according to claim 8, wherein said further predetermined range is between 5 micron and 10 micron.

10. The spray device according to claim 1, wherein said actuator is configured and intended to charge and release a dosed quantity of said first liquid and said further liquid in predetermined amounts.

11. The spray device according to claim 1, wherein said first reservoir is at least partly filled with said first liquid, said first liquid containing nicotine as an active compound, and wherein said further reservoir is at least partly filled with said further liquid, said further liquid containing one or more of a fragrance, flavouring and pigment.

12. The spray nozzle device according to claim 1, wherein said average cross section and said further average cross section is are substantially circular cross sections.

13. The spray nozzle device according to claim 1, wherein said first spray orifices have a substantially identical length and said further spray orifice have a substantially identical further length.

14. The spray device according to claim 1, wherein said layer and said further layer comprise a material that is taken from a group of silicon, silicon nitride and silicon oxide.

\* \* \* \* \*